US008691595B2

(12) United States Patent
Bergmann et al.

(10) Patent No.: US 8,691,595 B2
(45) Date of Patent: Apr. 8, 2014

(54) METHOD FOR DETECTING ANALYTES

(75) Inventors: Andreas Bergmann, Berlin (DE); Joachim Struck, Berlin (DE)

(73) Assignee: B.R.A.H.M.S. GmbH, Henningsdorf (DE)

( * ) Notice: Subject to any disclaimer, the term of this patent is extended or adjusted under 35 U.S.C. 154(b) by 825 days.

(21) Appl. No.: 12/666,024

(22) PCT Filed: Jun. 20, 2008

(86) PCT No.: PCT/EP2008/057913
§ 371 (c)(1), (2), (4) Date: Oct. 12, 2010

(87) PCT Pub. No.: WO2009/000784
PCT Pub. Date: Dec. 31, 2008

(65) Prior Publication Data
US 2011/0020833 A1    Jan. 27, 2011

(30) Foreign Application Priority Data

Jun. 22, 2007  (DE) .................. 10 2007 029 766
Aug. 4, 2007   (DE) .................. 10 2007 037 068

(51) Int. Cl.
*G01N 33/549* (2006.01)

(52) U.S. Cl.
USPC ........... 436/532; 436/518; 436/524; 436/164; 436/166; 435/7.1; 435/283.1; 435/287.1; 435/287.2; 435/288.7

(58) Field of Classification Search
USPC ........... 436/532, 518, 524, 164, 166; 435/7.1, 435/283.1, 287.1, 287.2, 288.7
See application file for complete search history.

(56) References Cited

U.S. PATENT DOCUMENTS

| | | | |
|---|---|---|---|
| 5,856,083 A * | 1/1999 | Chelsky et al. ............... 435/4 |
| 6,348,318 B1 | 2/2002 | Valkirs | |
| 6,723,510 B2 * | 4/2004 | Lubenow et al. ........... 435/6.16 |
| 7,361,473 B2 | 4/2008 | Valkirs et al. | |
| 7,825,227 B2 * | 11/2010 | Boniface et al. ............ 530/412 |
| 2001/0031473 A1 * | 10/2001 | Dattagupta et al. ............. 435/6 |
| 2002/0013003 A1 * | 1/2002 | Wagner et al. ............... 436/518 |
| 2002/0164659 A1 * | 11/2002 | Rao et al. .................... 435/7.5 |
| 2003/0108972 A1 * | 6/2003 | Zweig ....................... 435/7.92 |
| 2003/0218130 A1 * | 11/2003 | Boschetti et al. ............ 250/288 |
| 2004/0077024 A1 * | 4/2004 | Holmberg .................... 435/7.5 |
| 2004/0106173 A1 * | 6/2004 | Verde et al. ................. 435/69.1 |
| 2004/0171095 A1 * | 9/2004 | Schlatterer et al. ............ 435/15 |
| 2006/0211055 A1 | 9/2006 | Hafeman et al. | |
| 2008/0064113 A1 * | 3/2008 | Goix et al. .................... 436/86 |

FOREIGN PATENT DOCUMENTS

| | | |
|---|---|---|
| EP | 0303229 A2 | 2/1989 |
| WO | 9216841 A1 | 10/1992 |

OTHER PUBLICATIONS

The International Bureau of WIPO. "Written Opinion." PCT/EP2008/057913. Applicant: Brahms Aktiengesellschaft, et al. Mailed Jan. 21, 2010.
Richards, A. M., et al., "Plasma N-Terminal Pro-Brain Natriuretic Peptide and Adrenomedullin: New Neurohormonal Predictors of Left Ventricular Function and Prognosis After Myocardial Infarction," Circulation—Journal of the American Heart Association, 1998; 97; 1921-1929—Downloaded from circ.ahajournals.org on Jan. 19, 2010.
Qi, Y. F., et al., "Effects of Different Peptide Fragments Derived from Proadrenomedullin on Gene Expression of Adrenomedullin Gene," Peptides 23 (2002) 1141-1147.

* cited by examiner

*Primary Examiner* — Melanie Y Brown
(74) *Attorney, Agent, or Firm* — Millen, White, Zelano, Branigan, P.C.

(57) ABSTRACT

The subject of this invention is a process for detection of analytes from biological samples comprising the following process steps:
a) Preparation of a reversible binding partner 1 that is immobilized on a solid phase, to which an analyte binder is reversibly bonded via a reversible binding partner 2 that is bonded to the analyte binder, whereby the analyte binder is immobilized by binding between the reversible binding partners 1 and 2,
b) Addition of the biological sample and binding of the analyte to the reversible immobilized analyte binder in the case that the biological sample contains the analytes,
c) Separation of the biological sample,
d) Addition of a dissolving buffer, which dissolves the binding between the reversible binding partners 1 and 2, whereby the binding of the analyte to the analyte binder remains optional, and
e) Detection of the analyte in the dissolving buffer in the case that the biological sample contains the analytes and determination of the absence of the analyte in the case that the biological sample does not contain the analytes, respectively.

11 Claims, 3 Drawing Sheets

METHOD FOR DETECTING ANALYTES

The subject of this invention is a process for detection of analytes from biological samples comprising the following process steps:
- a) Preparation of a reversible binding partner 1 that is immobilized on a solid phase, to which an analyte binder is reversibly bonded via a reversible binding partner 2 that is bonded to the analyte binder, whereby the analyte binder is immobilized by binding between the reversible binding partners 1 and 2,
- b) Addition of the biological sample and binding of the analyte to the reversible immobilized analyte binder in the case that the biological sample contains the analytes,
- c) Separation of the biological sample,
- d) Addition of a dissolving buffer, which dissolves the binding between the reversible binding partners 1 and 2, whereby the binding of the analyte to the analyte binder remains optional, and
- e) Detection of the analyte in the dissolving buffer in the case that the biological sample contains the analyte or determination of the absence of the analyte in the case that the biological sample does not contain the analyte.

Quick-test or point-of-care (POC) testing processes have been developed in various technologies (1). The least of these have reached readiness for marketing, however.

Quick-test processes established nowadays, such as, e.g., the TRIAGE system (Biosite, San Diego, USA), but in particular the most popular process, immunochromatography, disadvantageously have a lower analytical sensitivity as well as reduced precision compared to standard immunoassays—to be processed manually or in an automated manner—but can advantageously process unprocessed whole-blood samples, in any case in suitable embodiments (2)-(7).

The drawbacks are due primarily to the sample matrix dependency of the process and the limitation of the usable sample volume.

The object of this invention is therefore to develop a process that is to be performed, i.a., as a quick test, which can process unprocessed whole-blood samples and which has analytical sensitivity and precision, which is comparable to that of standard immunoassays.

The subject of this invention is in particular the use of a reversible binding system according to the invention for the immobilization of an analyte-specific binder, e.g., anti-PCT antibody.

The subject of this invention is thus a process for the detection of analytes that consist of biological samples comprising the following process steps:
- a) Preparation of a reversible binding partner 1 that is immobilized on a solid phase, to which an analyte binder is reversibly bonded via a reversible binding partner 2 that is bonded to the analyte binder, whereby the analyte binder is immobilized by binding between the reversible binding partners 1 and 2,
- b) Addition of the biological sample and binding of the analyte to the reversible immobilized analyte binder in the case that the biological sample contains the analyte,
- c) Separation of the biological sample,
- d) Addition of a dissolving buffer, which dissolves the binding between the reversible binding partners 1 and 2, whereby the binding of the analyte to the analyte binder remains optional, and
- e) Detection of the analyte in the dissolving buffer in the case that the biological sample contains the analyte or determination of the absence of the analyte in the case that the biological sample does not contain the analyte.

It is clear to one skilled in the art that between steps b) and c), a certain incubation time is to be kept. The incubation time should not be shorter than 30 seconds and not longer than 24 hours; especially preferably within the framework of a quick-test process, an incubation time is between 5 and 15 minutes. The dissolving process according to step d) can preferably be up to 24 hours; preferably within the framework of a quick-test process, the dissolving process is longer than 15 seconds and shorter than 15 minutes, preferably between 5 and 15 minutes.

The binding of the analyte to the analyte binder remains during and/or after the dissolution according to d) or not at all. Both options are conceivable according to the invention. The binding between the analyte and the analyte binder preferably persists during and/or after the addition of the dissolving buffer according to d). The binding preferably persists at at least 90% of the analyte molecules. If the binding does not persist, it is preferably established again at a later time. Most preferably, the binding between analyte and analyte binder exists at the time of detection, i.e., it either persists during the dissolving process or is established again.

In a preferred embodiment, the analyte binder is an anti-analyte antibody.

In a preferred embodiment of the process according to the invention, the biological liquid is an unprocessed whole-blood sample.

According to the invention, the immobilized reversible binding partner 1 is immobilized directly or by means of a carrier protein. An exemplary carrier protein is BSA (bovine serum albumin). Suitable carrier proteins are known to one skilled in the art.

According to the invention, various binding partners are suitable that can form solid bonds, but under certain conditions however, they can break, these bonds and thus represent a "reversible binding system." Of special interest here are binding systems in which the binding can be destabilized by relatively mild conditions, i.e., conditions that do not significantly impair the conformation of proteins, in particular antibodies, and their binding to an antigen.

The application of such reversible binding systems is known in connection with purification possibilities of recombinant proteins from complex protein mixtures, such as, for example, cell extracts. By means of recombinant DNA technology, in this connection, the cDNA sequence that codes for the protein of interest is attached to a sequence that codes for a so-called "tag," so that a protein that is extended by a "tag" is expressed. Via a binding partner for the "tag" that is immobilized on a solid phase, the "tag" protein from the protein mixture can then be selectively bonded and then separated again from the solid phase by a specific destabilization of the "tag" bond. The protein of interest is then in enriched form or is pure in solution. Lists of commonly used "tags," corresponding immobilized binding partners, and specific destabilization methods are found in, e.g., (8)-(10).

Such binding systems can be used within the framework of the current invention as binding partners.

Within the framework of the process according to the invention, in particular the binding pair of reversible binding partners 1 and 2 can be selected from one of the following binding pairs:
- a) Positively- and negatively-charged peptide oligomers,
- b) $Ca^{2+}$-binding peptide/protein and antibody that the peptide/protein binds with higher affinity, when the peptide/protein has bonded $Ca^{2+}$,
- c) Oligohistidine (e.g., 6His) and Ni-NTA,
- d) Biotin and avidin or streptavidin or neutravidin.

Some reversible binding systems, which are within the framework of this invention, can be presented here briefly:

An example of a $Ca^{2+}$-binding peptide/protein and an antibody that binds the peptide-protein with higher affinity, when the peptide/protein has bonded $Ca^{2+}$, is the FLAG/M1 system, whereby the $Ca^{2+}$-binding peptide/protein is a FLAG-peptide and the antibody is an M1 antibody. In another system, the $Ca^{2+}$-binding peptide/protein is a protein C peptide and the antibody is an HPC4 antibody.

a) FLAG/M1

An example is thus the binding between the monoclonal antibody M1 (also described as 4E11) and the so-called FLAG peptide. This peptide can bind calcium$^{2+}$ and thus assumes a certain conformation. Only this conformation is bonded efficiently by M1. By adding calcium$^{2+}$-complexing agents, such as, for example, EDTA, calcium$^{2+}$ is removed from the peptide, and the peptide assumes another conformation, by which the M1 antibody drastically reduces its affinity to peptide; U.S. Pat. No. 4,851,341 (11).

b) C/HPC4 Protein

Another, analogous example of such a binding pair is a peptide that is derived from human protein C and that also can assume a calcum$^{2+}$-dependent shape, and the monoclonal antibody HPC4 (12).

c) $Ni^{2+}$-NTA/6 His

Another example is the $Ni^{2+}$-NTA/6 His system, which can be destabilized specifically by the addition of imidazole (13).

d) Charged Peptide Oligomers

Another example is a binding pair of positively- or negatively-charged peptide oligomers, such as, e.g., oligo-Lys or oligo-Asp, whose binding to one another can be destabilized by increasing the ionic strength. As a binding pair, a charged peptide oligomer is described in connection with an ion-exchange matrix; also, this binding is to be destabilized by increasing the ionic strength (14)-(16).

In addition to reversible binding systems, in which one of the binding partners is integrated in a recombinant protein, systems are also known in which one of the binding partners is conjugated chemically to the protein that is to be immobilized. For example, the biotin/avidin system can be mentioned here. Biotin can be conjugated, e.g., in the form of an NHS ester to primary amine groups of one protein (17). This binding system can also be destabilized by adding excess biotin, but only under drastic conditions such as elevated temperature and extended incubation time (18). A variant of this system is described, however, which uses so-called monomeric avidin; after saturation of "non-reversible" binding sites with biotin, the remaining "reversible" binding sites are suitable to bind a biotinylated protein, which then can be dissolved under mild conditions by means of biotin from the binding site (19).

Peptide "tags," as described above for recombinant proteins, should also be chemically conjugatable to a protein, whereby the thus derivatized protein can then be applied to a reversible binding. Within the framework of this invention, the chemical conjugation can be viewed as a preferred variant of the protein derivatization, since the degree of derivatization can be controlled, and the chemical conjugation is comparatively time-saving and economical.

All previously mentioned examples of reversible binding systems are based on a non-covalent interaction of the binding partners. Within the framework of this invention, however, those systems can also be regarded as reversible binding systems in which first a covalent bond is present and which then can be chemically dissolved. By way of example, there can be mentioned here the covalent cross-linking by means of a cleavable hetero-bifunctional cross-linker, such as, for example, SPDP (20); by adding a reducing agent, the disulfide bride can be cleaved, and the bond can thus be dissolved.

The subject of the invention is thus also the quick-test process according to the invention, whereby the analyte binder is bonded covalently to the reversible binding partner 2.

The subject of this invention is thus the process according to the invention in a preferred embodiment, whereby the analyte binder is an anti-procalcitonin antibody.

A preferred subject of the invention is thus the application of a reversible binding system for the immobilization of an analyte-specific binder, e.g., anti-PCT antibody.

The application is formulated below by way of example for the reversible binding system of the charged peptide oligomers (see above), but can be transferred analogously for the other systems. Oligo-Asp is conjugated on a carrier protein as bovine serum albumin (BSA), and this conjugate is immobilized in a stable manner on a solid phase, such as, e.g., high-binding polystyrene microtiter plates. Oligo-Lys is conjugated on an anti-PCT antibody. Incubation of the oligo-Lys-anti-PCT antibody with the solid phase results in an immobilization of the antibody by binding between the oligo-Lys and oligo-Asp portions by ionic interaction.

In an alternative embodiment, the anti-PCT antibody can also be immobilized indirectly by means of an oligo-Lys-derivatized antibody against the anti-PCT antibody (for example, an anti-mouse IgG antibody, if the anti-PCT antibody is a mouse-monoclonal antibody).

The principle of immune extraction is explained by way of example below for the PCT analysis:

First, an anti-PCT antibody is immobilized via a reversible binding system on a solid phase. A whole-blood sample that is to be examined (charged peptide oligomers and EDTA blood for this example) is added, and PCT is immune-extracted from the sample. In this case, a comparatively large volume of sample can be used, so that a comparatively large amount of PCT can be extracted, which results below in a high analytical sensitivity of the test. After a short incubation time, the sample is separated (by washing or other suitable separating methods, such as, for example, suctioning-off or suitable centrifuging). In the next step, a buffer is added ("dissolution buffer"), which contains an agent (e.g., the strongly negatively-charged heparin in the oligo-Lys-/oligo-Asp system), which is suitable for destabilizing to a large extent the binding of the antibody to the solid phase, but not the binding between PCT and antibody. Thus, a solution is available that contains the analytes to be determined (complexed on a specific antibody) in a large amount. The solution for any sample that is examined is always of identical composition since the sample matrix was separated in advance. The advantages of this step thus consist in:

The possibility of using unprocessed whole blood,

The possibility of using larger sample volumes so that relatively large amounts of analytes can be extracted and ultimately a high analytical assay sensitivity in subsequent determination processes can be achieved, The matrix independence for following steps in the determination process that have an advantageous effect on precision and correctness of the determination process.

The immune-extracted analyte that is brought into solution can be detected by various methods. One example is the TRACE technology, and another (additional method explained below) is immunochromatography.

For a sandwich immunoassay, the TRACE technology uses two antibodies, which are labeled with different fluorescence labels (for example, cyanin or cryptate). In sandwich formation with the analyte in solution, both labels achieve a proximity in space that leads to a specific light emission according to corresponding light excitation.

In connection with the analysis of PCT by way of example, the anti-PCT antibody that is conjugated with oligo-Lys is first labeled in addition with cryptate before the immobilization.

Herewith, the immune extraction is done. In the dissolution buffer, the second cyanin-labeled anti-PCT antibody that is necessary for the sandwich formation is now contained in addition to the dissolving agent. Thus, by adding the dissolution buffer, it results both in dissolving the antigen-antibody complex from the solid phase and in sandwich formation, which can be detected after suitable light excitation. Dissolution and addition of the second antibody to the sandwich formation can also be done sequentially.

In an above-described variant, the analyte-specific antibody can be immobilized indirectly via an oligo-Lys-derivatized, e.g., anti-mouse IgG antibody before the immune extraction. In this embodiment, the fluorescence label can then be conjugated to one or the other antibody.

In the example of immunochromatography, the anti-PCT antibody that is conjugated with oligo-Lys is first labeled in addition with biotin before the immobilization. Herewith, the immune extraction is done. In the dissolution buffer, now in addition to the dissolving agent, the second anti-PCT antibody that is labeled with colloidal gold and that is necessary for the sandwich formation is now included. Dissolution and addition of the second antibody to the sandwich formation can also be done sequentially. The reaction mixture is then applied to an immunochromatographical test strip, onto which as a trap for the sandwich that is formed, a biotin binder such as, e.g., avidin, is sprayed crosswise to the feed direction of the reaction solution as a fine line in the rear area of the test strip.

In an especially preferred embodiment of the process according to the invention, the analyte binder is labeled and also remains labeled with a label for the detection of the analyte after the addition of the dissolving buffer.

In the embodiment of immunochromatography, the following additional variants can be conceivable:

In addition to the derivatization with binding partners 2, the immune-extraction antibody is additionally biotinylated. A second antibody for the sandwich formation is labeled (e.g., with colloidal gold). The trap on the test strip would then be a biotin binder such as avidin or streptavidin or neutravidin.

The immunoextraction antibody (e.g., polyclonal sheep) is derivatized only with binding partner 2. A second antibody for sandwich formation had to originate from another animal species (e.g., monoclonal mouse) and is labeled (e.g., with colloidal gold).

The trap on the test strip would then be an anti-sheep IgG antibody. Both variants are also conceivable in the form that the immunoextraction antibody carries the labeling and whereby in the first variant, the second antibody is then biotinylated (as an alternative, here, the second antibody could also be sprayed directly on the strip).

In another preferred embodiment of the process, the dissolving buffer contains another labeled component that is necessary for the detection.

In an especially preferred embodiment of the process, the additional labeled component that is necessary for the detection is a second analyte binder for the implementation of a sandwich immunoassay.

The detection of the labeled analyte is especially preferably done by an immunoassay with use of TRACE technology.

In another preferred embodiment, the detection of the labeled analyte is done by means of immunochromatography.

In an especially preferred variant according to the invention, the biological sample is undiluted and is used in such a volume that the coated portion of the solid phase is brought completely into contact with the biological sample.

The period of adding the sample until it is detected especially preferably does not exceed 30 minutes, and the process can thus be considered to be a quick-test process.

Also a subject of this invention is a device for implementing the process according to the invention, comprising:

A solid phase with a reversible binding partner 1 immobilized therein, to which an analyte binder is reversibly bonded via a reversible binding partner 2 that is bonded to the analyte binder, Whereby the binding between the reversible binding partners 1 and 2 is dissolved by adding a dissolving buffer, but the binding of the analyte to the analyte binder remains optional when adding the dissolving buffer.

Likewise, the subject of this invention is a kit for implementing the process according to the invention, comprising:

A solid phase with an immobilized reversible binding partner 1,

A complex comprising analyte binder that is bonded to the reversible binding partner 2, whereby this complex optionally can already be present in immobilized form by binding the reversible binding partners 1 and 2 to the solid phase, Dissolving buffer, which dissolves the binding between the reversible binding partners 1 and 2, whereby the binding of the analyte to the analyte binder remains optional, however.

In an especially preferred embodiment, the analyte binder that is found in the kit is an anti-PCT antibody.

As a selected binding pair, the most preferred kit contains reversible binding partners 1 and 2 selected from one of the following binding pairs:

Positively- and negatively-charged peptide oligomers, $Ca^{2+}$-binding peptide/protein and antibody, which the peptide/protein binds with higher affinity when the peptide/protein has bonded $Ca^{2+}$, Oligohistidine (e.g., 6His) and Ni-NTA, Biotin and avidin or streptavidin or neutravidin.

The following examples are to explain the invention in more detail without limiting the subject of the invention:

EXAMPLES

Immune Extraction of PCT from Whole Blood

As a basis for the processing of additional steps, it was first examined whether and how effectively an analyte, examined here in the PCT example, can be extracted from unprocessed EDTA whole blood by means of an analyte-specific antibody that is immobilized on a solid phase. After a short incubation (5 minutes) and separation of the whole-blood sample, the bonded PCT was detected with a second, chemiluminescence-labeled anti-PCT antibody. For comparison, PCT-containing serum, diluted in buffer, was incubated on the same solid phase, but longer (2 hours), and the bonded PCT was detected as above after separation from the dilute sample.

In particular, the test was performed as follows:

To determine the immune extraction, the components from the BRAHMS PCT-sensitive LIA Kit were used (BRAHMS Aktiengesellschaft, Hennigsdorf, Germany). The luminescence-labeled anti-PCT tracer antibody A was dissolved in the tracer reconstitution buffer B according to operating instructions. A standard series was dissolved in EDTA whole blood of a healthy blood donor at the following concentrations: c=0.007; 0.014; 0.036; 0.171; 0.383; 1.73; 7.99 ng/ml. In the tubes that are coated with anti-PCT antibodies, 300 µl each of whole-blood standard was pipetted and incubated for 5 minutes at room temperature. Then, the tubes were washed with 5×1 ml of washing solution (8 mM Tris, 60 mM NaCl, 0.2% of Tween 20, pH 7.5). Then, 200 µl of luminescence-labeled anti-PCT antibody was pipetted and incubated for 2 hours at room temperature; the tubes were washed once more with 5×1 ml of washing solution. The chemiluminescence bonded to the tubes was measured in a luminometer (BERTHOLD Company, BAD WILDBAD, GERMANY, LB952T; base reagents from BRAHMS AG).

The reference method (determination of PCT from dilute serum) was performed as follows based on the BRAHMS PCT-sensitive LIA Kit (BRAHMS Aktiengesellschaft, Hennigsdorf, Germany): A standard series was dissolved in null serum from the test kit at the following concentrations: c=0; 0.008; 0.031; 0.042; 0.126; 0.251; 1.21; 5.61; 28.0 ng/ml. In the tube that is coated with anti-PCT antibody, 50 µl each of serum standard and 250 µl of tracer reconstitution buffer B was pipetted and incubated for 2 hours at room temperature. Then, the tubes were washed with 5×1 ml of washing solution (8 mM Tris, 60 mM NaCl, 0.2% Tween 20, pH 7.5). Then, 200 µl of luminescence-labeled anti-PCT antibody was pipetted and incubated for 2 hours at room temperature; the tubes were washed once more with 5×1 ml of washing solution. The chemiluminescence bonded to the coated tubes was measured in a luminometer (BERTHOLD Company, BAD WILDBAD, GERMANY, LB952T; base reagents from BRAHMS AG) (FIG. 1).

Production of Antibodies to be Bonded Reversibly to a Solid Phase

Several of the reversible binding systems described further above were examined for their suitability for binding an antibody, here in the example an anti-PCT antibody, reversibly to a solid phase. In this respect, the antibody was derivatized to different degrees (see Table 1) and labeled with a chemiluminescence label. Thus, it was examined how these antibodies bind to solid phases corresponding to the respective derivative and how they can be dissolved again. The summary of the results in Table 1 shows that all examined reversible binding systems with the exception of the biotin/avidin system can be destabilized specifically and quickly and—with limitations for the 6His/Ni-NTA system—are unimpaired by the blood matrix.

In addition, it was observed that the efficiency of the binding and specific dissolution can be affected by the respective degree of derivatization (the molar ratio of binding partner 1 per antibody), the concentration of the binding partner 2 that is immobilized on the solid phase, thus whether binding partner 1 was conjugated to the antibody and binding partner 2 was immobilized, or binding partner 2 was conjugated to the antibody and binding partner 1 was immobilized, and in the case of the oligo-Asp/oligo-Lys system, the length of the two oligomers. Therefore, within the framework of this invention, such variants also fall under the term of reversible binding systems, and the claims expressly include such variants, but the variants that are described by way of example here can be considered to be preferred embodiments. As alternatives to the oligo-Lys-BSA, polylysine solid phases have also proven suitable.

In particular, the test was performed as follows:

Binding Partner 1 (Liquid Phase)

1. Production of MACN-Chemiluminescence-Labeled Antibody

A polyclonal anti-calcitonin sheep antibody was treated as follows:

Three labels were prepared; the latter were buffered differently after the incubation (see below).

For chemiluminescence labeling of the antibody, 1 ml of the antibody solution (c=3.19 mg/ml) was mixed with 40 µl of 1 M potassium phosphate, pH 7.8, and with 2.7 µl of MACN-acridinium-NHS ester (c=1 mg/ml; InVent Company GmbH, Hennigsdorf, Germany), (molar labeling ratio of antibody: MACN 10:1). Then, it was incubated for 30 minutes at room temperature. Then, the labeling preparations were buffered in 1.5 ml of mobile solvent via NAP-10 gel filtration columns (Pharmacia, Upsalla, Sweden), and thereby low-molecular components were removed:

| Label 1 | PBS | pH 7.4 for biotinylation | see 2.1. |
|---|---|---|---|
| Label 2 | 100 mM sodium phosphate, 5 mM EDTA | pH 6.9 for SPDP activation | see 2.2. |
| Label 3 | PBS, 10 mM EDTA | pH 8.0 for SMCC activation | see 2.3. |

The protein content was determined by photometry; the labeled antibodies were stored in portions at −20° C.

TABLE 1

| Derivative of an Antibody (Binding Partner 1) | Solid Phase (Binding Partner 2) | Dissolution Agent | Proportion of the Non-Specific Antibody that can be Dissolved by Blood (10 Minutes of Incubation) Relative to the Previously Bonded Amount | Proportion of the Antibody that can be Dissolved by Dissolution Agent (10 Minutes of Incubation) Relative to the Previously Bonded Amount | Proportion of the Antibody that can be Dissolved by Dissolution Agent (30 Minutes of Incubation) Relative to the Previously Bonded Amount |
|---|---|---|---|---|---|
| Biotin | Avidin | 25 mM Biotin | 0.7% | 1.9% | 2.5% |
| M1 Antibody | FLAG-Peptide-BSA | 10 mM EDTA | 7.8% | 58.7% | 74.8% |
| 6His | Ni-NTA | 250 mM Imidazole | 38.6% | 89.4% | 98.8% |
| HPC4 Antibody | Protein C-Peptide-BSA | 10 mM EDTA | 3.5% | 38.3% | 69.2% |
| Oligo-Asp | Oligo-Lys BSA | 0.01% Heparin | 5.3% | 80.0% | 93.2% |

2. Derivatizations of MACN-Chemiluminescence-Labeled Antibodies

2.1. Biotinylation

The MACN antibody was biotinylated with EZ-Link NHS-Chromogenic-Biotin (Pierce Company, Rockford, Ill., USA, Art. No. 21325) at a molar ratio 1:10.

1 mg of MACN antibody was mixed with 5.41 µl of 1.233 mM biotin solution (freshly dissolved in DMSO) and incubated for 60 minutes at room temperature. The reaction was stopped for 10 minutes at room temperature with 100 µl of 50 mM glycine and purified on an NAP5 column (Pharmacia, Upsalla, Sweden).

For separating the last radicals from biotin that is not bonded to antibodies, a gel-filtration HPLC was performed (column: Bio-Sil Sec 400, Biorad Company, Munich, Germany). The sample was applied and chromatographed at a flow rate of 0.8 ml/min with PBS, pH 7.4. The wavelengths of 280 nm and 354 nm were measured with a flow photometer. The µM of biotin/µM of antibody degree of labeling was 0.48 at the peak. The antibody-containing fractions (retention time 11-12 minutes) were pooled.

The protein content was determined by photometry; the conjugate was stored in portions at −20° C.

2.2 Conjugation with Anti FLAG-tag M1 Antibodies and Anti ProtC-tag HPC4 Antibodies, Respectively For the conjugation with anti FLAG-tag M1 (Sigma Company, Deisenhofen, Germany, Art. No. F 3040) and anti ProtC-tag HPC 4 (Roche Company, Nutley, N.J., USA, USA, Art No. 11814516001) antibodies respectively, the latter and the MACN antibody were activated with SPDP (N-succinimidyl 3-(2-pyridyldithio)propionate, Pierce Company, Rockford, Ill., USA, Art. No. 21857) at a molar ratio 1:7 (see "SPDP Reagents Instructions," Pierce, Rockford, Ill., USA).

Each 2 mg of antibody was mixed with 4.67 µl, 20 mmol of SPDP (freshly dissolved in ethanol) and incubated for 30 minutes at room temperature. Only the activated M1 and HPC4 antibodies were set with 200 mmol of DTT (dithiothreitol, dissolved in 100 mmol of sodium phosphate, 5 mmol of EDTA, pH 6.9) to a final concentration of 10 mmol of DTT and reduced for 15 minutes at room temperature.

The reduced M1 and HPC4 antibodies, respectively, were in each case purified on an NAP10 column (mobile solvent: 100 mmol of sodium phosphate, 5 mmol of EDTA, pH 6.9), and the protein content was determined by photometry.

The reduced products were conjugated in each case with the non-reduced SPDP-activated MACN antibodies at a molar ratio 1:1 overnight at 4° C. Then, the reaction was stopped for 10 minutes with 50 µl, 100 mmol of cysteine each.

The protein content was determined by photometry; the conjugates were stored in portions at −20° C.

2.3. Conjugation with His-tag and Oligo-Asp Peptide, Respectively

For coupling of the His-tag peptide "PRG12" (amino acid sequence RGSHHHHHHGGC (SEQ ID NO. 1), JPT Company GmbH, Berlin, Germany, M=1359.8) and the oligo-Asp peptide "D14C" (amino acid sequence DDDDDDDDDDDDDC (SEQ ID NO. 2), JPT Company GmbH, Berlin, Germany, M=1731.43), respectively, the MACN antibody was activated with SMCC (succinimidyl 4-(N-maleimidomethyl)-cyclohexane-1-carboxylate, Pierce Company, Rockford, Ill., USA, Art. No. 22360) at a molar ratio 1:50 (see "SMCC and Sulfo-SMCC Instructions," Pierce, Rockford, Ill., USA).

2 mg of MACN antibody was mixed with 6.68 µl of 100 mM SMCC (freshly dissolved in DMSO) and incubated for 30 minutes at room temperature. The product was purified on an NAP10 column (Pharmacia, Upsalla, Sweden) (mobile solvent: PBS, 10 mmol of EDTA, pH 8) and the protein content was determined by photometry.

Then, the conjugation immediately took place with the His-tag, or oligo-Asp peptide (dissolved in distilled water) at a molar ratio 1:100. After incubation for 60 minutes at room temperature, the reaction was stopped for 10 minutes with 100 µl of 100 mM cysteine, purified once more on an NAP25 column (Pharmacia, Upsalla, Sweden) (mobile solvent: PBS, pH 7.4), and the protein content was determined by photometry.

Both conjugates were stored aliquoted at −20° C.

Binding Partner 2 (Solid Phase)

1.1 Conjugation of BSA with FLA-tag/ProtC-tag

For coupling the Flag-tag peptide "PDC12" (amino acid sequence DYKDDDDKGGGC, (SEQ ID NO. 3), JPT Company GmbH, Berlin, Germany, M=1286.46) and ProtC-tag peptide PEG15 (amino acid sequence EDQVD-PRLIDGKGGC, (SEQ ID NO. 4), JPT Company GmbH, Berlin, Germany, M=1601.7), respectively, protease-free bovine serum albumin (Sigma Company, Deisenhofen, Germany) was activated with SMCC (succinimidyl 4-(N-maleimidomethyl)cyclohexane-1-carboxylate, Pierce Company, Rockford, Ill., USA, Art. No. 22360) at a molar ratio 1:2 (see "Instructions SMCC and Sulfo-SMCC," Pierce, Rockford, Ill., USA).

2500 µl of 0.5% BSA (dissolved in PBS, 10 mmol of EDTA, pH 8) was mixed with 3.78 µl of 100 mM SMCC (freshly dissolved in DMSO) and incubated for 30 minutes at room temperature. The product was purified on an NAP25 column (Pharmacia, Upsalla, Sweden) (mobile solvent: PBS, 10 mmol of EDTA, pH 8), and the protein content was determined by photometry.

Then, the conjugation took place immediately with the FLAG-tag or ProtC-tag peptide (dissolved in distilled water) at a molar ratio 1:100. After incubation for 60 minutes at room temperature, the conjugates were stopped for 10 minutes each with 100 µl of 100 mM cysteine and purified once more on an NAP25 column (Pharmacia, Upsalla, Sweden) (mobile solvent: PBS, pH 7.4); the protein content was determined by photometry.

The BSA+FLAG-tag and BSA+ProtC-tag conjugate was stored aliquoted at −20° C.

1.2 Conjugation of BSA with Oligo-Lys Peptide

For coupling the oligo-Lys peptide "K14C" (amino acid sequence KKKKKKKKKKKKKKC, (SEQ ID NO. 5), JPT Company GmbH, Berlin, Germany, M=1914.27), protease-free bovine serum albumin (Sigma Company, Deisenhofen, Germany) was activated with SMCC at a molar ratio 1:25.

1000 µl of 0.5% BSA (dissolved in PBS, 10 mmol of EDTA, pH 8) was mixed with 18.9 µl of 100 mM SMCC (freshly dissolved in DMSO), and incubated for 30 minutes at room temperature. The product was purified on an NAP10 column (Pharmacia, Upsalla, Sweden) (mobile solvent: PBS, 10 mmol of EDTA, pH 8), and the protein content was determined by photometry.

Then, the conjugation immediately took place with the oligo-Lys peptide (dissolved in distilled water) at a molar ratio 1:100. After incubation for 60 minutes at room temperature, the reaction was stopped for 10 minutes with 100 µl of 100 mM cysteine, purified once more on an NAP25 column (Pharmacia, Upsalla, Sweden) (mobile solvent: PBS, pH 7.4), and the protein content was determined by photometry.

The BSA+oligo-Lys conjugate was stored aliquoted at −20° C.

2. Coupling of the Conjugates and Avidin, Respectively

Irradiated star tubes (Greiner Company, Frickenhausen, Germany) were coated as follows with the conjugates from 1.1 and 1.2, and with avidin (Pierce, Rockford, Ill., USA, Art. No. 21121, dissolved in distilled water), respectively:

The components were diluted with a solution of 10 mM Tris, 100 mM NaCl, pH 7.8 to a concentration of 6.67 µg/ml. 300 µl each of the solutions was pipetted per tube and incubated for 20 hours at 22° C. The solutions were suctioned off. Then, each tube was saturated with 300 µl of 0.5% bovine serum albumin, 2% Karion FP for 2 hours and suctioned off once more. Then, the tubes were dried in a vacuum dryer and stored at 4° C.

3. Ni-NTA Solid Phase

Ni-NTA microtiter plates (Qiagen Company, Hilden, Germany, Art. No. 1006387) were used.

4. Assay for Detecting Reversibly-Bonded Antibodies 4.1 Binding of MACN-Antibody Conjugates The MACN-antibody conjugates were set at a concentration of 1.5 µg/ml with dilution buffer (see Table 2). 300 µl each were pipetted into several parallel batches in the corresponding solid phase and incubated overnight at room temperature. The tubes were washed with 5×1 ml, the Ni-NTA microtiter plate with 5×300 µl of washing buffer (see Table 2).

In one each of the batches, the amount of bonded MACN-antibody conjugate was determined:

The amount of MACN-antibody conjugate bonded to the tubes was measured in a luminometer (BERTHOLD Company, BAD WILDBAD, GERMANY, LB952T; base reagents from BRAHMS AG). The amount of MACN-antibody conjugated bonded to the microtiter plate was measured in a microplate luminometer (BERTHOLD Company, BAD WILDBAD, GERMANY, MPL2; base reagents from BRAHMS AG).

4.2 Measurement of the Non-Specific Dissolution of the MACN-Antibody Conjugates with Whole Blood In additional batches of the bonded MACN-antibody conjugates, 300 µl each of whole blood (see Table 2) was pipetted and incubated for 10 minutes. The tubes were washed with 5×1 ml, the Ni-NTA microtiter plate with 5×300 µl of washing buffer (see Table 2). The amount of MACN-antibody conjugate left in the tubes was measured in a luminometer (BERTHOLD Company, BAD WILDBAD, GERMANY, LB952T; base reagents from BRAHMS AG).

The amount of MACN-antibody conjugate left on the microtiter plate was measured in a microplate luminometer (BERTHOLD Company, BAD WILDBAD, GERMANY, MPL2; base reagents from BRAHMS AG).

4.3 Measurement of the Specific Dissolution of the MACN-Antibody Conjugates with Dissolution Buffer In additional batches of the bonded MACN-antibody conjugates, 300 µl each of dissolution buffer (see Table 2) was pipetted and incubated for 10 or 30 minutes. The tubes were washed with 5×1 ml of washing buffer, and the Ni-NTA microtiter plate was washed with 5×300 µl of washing buffer (see Table 2).

The amount of MACN-antibody conjugate left in the tubes was measured in a luminometer (BERTHOLD Company, BAD WILDBAD, GERMANY, LB952T; base reagents from BRAHMS AG).

The amount of MACN-antibody conjugate left on the microtiter plate was measured in a microplate luminometer (BERTHOLD Company, BAD WILDBAD, GERMANY, MPL2; base reagents from BRAHMS AG).

TABLE 2

| Solid Phase | MACN Antibody + | Dilution Buffer | Washing Buffer | Whole Blood | Dissolution Buffer |
|---|---|---|---|---|---|
| Avidin | Biotin | PBS pH 7.4 0.5% BSA | 8 mM Tris pH 7.5 60 mM NaCl, 0.2% Tween 20 | EDTA Whole Blood | PBS pH 7.4, 0.5% BSA, 25 mM Biotin |
| Ni-NTA | His-tag Peptide | | | | PBS pH 7.4, 0.5% BSA, 250 mM imidazole |
| Oligo-Lys BSA | Oligo-Asp Peptide | | | | PBS pH 7.4, 0.5% BSA, 0.6 M KF, 0.01% Heparin |
| FLAG-tag BSA | Anti FLAG-tag M1 | 50 mM HEPES pH 7.2 150 mM NaCl, 0.02% Tween, 0.5% BSA, 5 mM CaCl$_2$ | 50 mM HEPES pH 7.2 150 mM NaCl, 0.02% Tween 5 mM CaCl$_2$ | Heparin Whole Blood | 50 mM HEPES pH 7.2 150 mM NaCl, 0.02% Tween, 0.5% BSA, 50 mM EDTA |
| ProtC-tag BSA | Anti ProtC-tag HPC4 | | | | |

Further Studies on the Oligo-Asp/Oligo-Lys System

Dissolution Agents

As described above, an efficient dissolution of the bond by adding 0.01% heparin was achieved (see Table 1 and related description). As alternative dissolution agents, NaCl and KF were also studied. A comparable action with 0.01% heparin on the dissolution of the bond was achieved with NaCl or KF concentrations of >0.8 M. Numerous other variations in the buffer composition are conceivable, which result in the dissolution of the bond (other salts of low molecular weight, other charged oligomers or polymers, other pH values). All of these variations are defined as dissolution agents in terms of this invention. Those variations can be considered as especially preferred, however, which, on the one hand, efficiently destabilize the binding of the oligo-Asp/oligo-Lys system, but on the other hand leave the binding between antibody and analytes as unimpaired as possible. Heparin in a concentration of 0.01% represents such a preferred variant, since, of course, many immunoassays can use heparin plasma as a sample matrix, and the concentration of heparin in this plasma is typically in the range of 0.01%.

Specificity of the Bond of the Analyte to the Solid Phase

If a biological sample is added to a solid phase that is coated with oligo-Lys-BSA/oligo-Asp-analyte binder, there could be the worry that the analyte of interest from the sample would not only bind to the analyte-specific antibody but possibly also non-specifically via ionic interaction to optionally free lysine portions of the solid phase. If this was the case, the accuracy of the subsequent analyte detection (after the dissolving step) would be impaired. Whether and to what extent such non-specific analyte bondings can take place was studied by having various synthetic peptides, which are largely identical to known natural analytes, and therefore represent the latter, be chemiluminescence-labeled, diluted in a plasma matrix, and incubated in the tube, which was coated with oligo-Lys-OBSA, and an oligo-Asp-anti PCT antibody was bonded thereto. The detected portion of non-specifically bonded peptides was always below 7% of the peptide offered. Thus, non-specific analyte binding to the solid phase does not represent a problem.

In particular, the test was performed as follows:

1. Production of MaCN-Chemiluminescence-Labeled Peptides

The following peptides (all from the JPT Company GmbH, Berlin, Germany) were labeled with MACN:

"PPL41" (amino acid sequence PEVPPWTGEVS-PAQRDGGALGGGGRGPWDSSDRSALLKSKL, (SEQ ID NO. 6) derived from NT-proANP), "PSW44" (amino acid sequence SSEEHLRQTRSETMRNSVKSSFHDP-KLKGKPSRERYVTHNRAHW, (SEQ ID NO. 7), derived from proEndothelin), "PAY33" (amino acid sequence ATQLDGPAGALLLRLVQLAGAPEPFEPAQPDAY, (SEQ ID NO. 8) derived from copeptin), "Peptide 45-92" (amino acid sequence ELRMSSSYPTGLADVKAGPAQTLIRPQD-MKGASRSPEDSSPDAARIRV, (SEQ ID NO. 9) derived from pro-adrenomedullin).

For chemiluminescence labeling, the peptides at a molar ratio 1:1 were labeled with MACN-acridinium-NHS ester (InVent Company GmbH, Hennigsdorf, Germany) for 1 hour at room temperature. Then, the reaction was stopped for 10 minutes with 1 mM Tris, pH 7.8.

For separation of non-incorporated MACN, the labeling batches were purified on a reversed-phase C18 column (μBondapak, Waters WAT027342, No. 0202352581). The samples were applied and chromatographed at a flow rate of 1.0 ml/min by means of an increasing water/acetonitrile (+0.1% TFA) gradient. With a flow photometer, the wavelengths of 214 nm, 280 nm and 368 nm were measured, and the peaks were detected.

The labeled peptides were stored in portions at −20° C.

1.1. Production of BSA+Oligo-Lys Conjugate: See Above
1.2. Production of Anti-Calcitonin Sheep Antibody+Oligo-Asp Conjugate For coupling of the oligo-Asp peptide "D14C" (amino acid sequence DDDDDDDDDDDDDDC, (SEQ ID NO. 2), (JPT Company GmbH, Berlin, Germany, M=1731.43), a polyclonal anti-calcitonin sheep antibody ("anti-PCT antibody 1") was activated with SMCC at the ratio 1:25 (see "SMCC and Sulfo-SMCC Instructions," Pierce).

3 mg of antibody (in 4.5 ml of PBS, 10 mM EDTA, pH 8) was mixed with 5.0 μl of 100 mM SMCC (freshly dissolved in DMSO), and incubated for 30 minutes at room temperature. The product was purified on two NAP25 columns (mobile solvent: PBS, 10 mmol of EDTA, pH 8), and the protein content was determined by photometry.

Then, the conjugation was carried out immediately with the oligo-Asp peptide (dissolved in distilled water) at a molar ratio 1:100. After incubation for 60 minutes at room temperature, the reaction was stopped for 10 minutes with 100 μl of 100 mM cysteine, non-conjugated peptide was separated on NAP25 columns (mobile solvent: PBS, pH 7.4), and the protein content was determined by photometry.

The anti-calcitonin sheep antibody+oligo-Asp conjugate was stored aliquoted at −20° C.

2. Coupling of the Conjugates to Tubes
2.1. Coupling: BSA+Oligo-Lys Conjugate

Irradiated star tubes (Greiner Company, Frickenhausen, Germany) were coated with BSA-oligo-Lys conjugate as follows:

The conjugate was diluted in 10 mM Tris, 100 mM NaCl, pH 7.8 to form a concentration of 6.67 μg/ml. In each tube, 300 μl of this solution was pipetted and incubated for 20 hours at 22° C. The solution was suctioned off. Then, each tube was saturated with 300 μl of 0.5% bovine serum albumin, 2% Karion FP for 2 hours and suctioned off once more. Then, the binding of the anti-calcitonin sheep antibody+oligo-Asp conjugate was carried out:

2.2 Bond: Anti-Calcitonin Sheep Antibody+Oligo-Asp Conjugate

The conjugate was diluted in PBS, 0.5% protease-free BSA, pH 7.4, to a concentration of 667 ng/ml. 300 μl of this solution was pipetted into each tube and incubated for 1 hour at 22° C. The solution was suctioned off. Then, each tube was saturated once more with 300 μl of 0.5% bovine serum albumin, 2% Karion FP for 2 hours and then suctioned off.

Then, the tubes were dried in a vacuum dryer and stored at 4° C.

3. Determination of the Non-Specific Bond:

The MACN peptides were diluted in a plasma matrix. 300 μl each was pipetted into the tubes that were coated with the oligo-Lays-BSA and the oligo-Asp-anti-PCT antibody and incubated for 30 minutes at room temperature. The tubes were washed with 3×1 ml of PBS, pH 7.4, 0.5% protease-free BSA. The amount bonded to the tube as well as the total activity of MACN peptide used were measured in a luminometer (BERTHOLD Company, BAD WILDBAD, GERMANY LB9527; base reagents from BRAHMS AG). The percentage of non-specific binding relative to the total activity was:

| PSW44 | 3.0% |
| PPL41 | 3.1% |
| PAY33 | 6.5% |
| Peptide 45-92 | 2.9% |

Comparison to the PCT Example: Standard Immunochromatography from Whole Blood vs. Immune Extraction of PCT from Whole Blood, Dissolution and Analyte Detection by Means of Immunochromatography or TRACE Technology PCT (procalcitonin) was selected as a relevant model analyte. It is a marker for bacterial infections, in particular serious infections that result in a systemic inflammatory reaction of the host (sepsis) (21). Sandwich immunoassays for detection of PCT use antibodies against the calcitonin or catacalcin portion of the peptide (22), (23).

The immunochromatography represents the quick-test methodology for immunological detection of analytes from whole blood that is the most common in today's routine use and can therefore be referred to as "standard immuno-chromatography." This methodology was therefore selected here as a reference method to explain advantages of the principle according to the invention of immune extraction and dissolution ("immune transfer") with associated analyte detection. Two different detection methods were studied: on the one hand, the immunochromatography, and, on the other hand, the TRACE (time-resolved amplified cryptate emission) technology. With all three methods, PCT concentrations from PCT-containing whole-blood samples were determined in 10× determination in each case. In FIG. 2, the resulting precision profiles of the methods are contrasted. It is clear to see that both methods, which are subjects of this invention, thus yield immune transfers in connection with a detection method (it is immunochromatography or TRACE technology), essentially more precise and sensitive measuring results than the reference method (standard immuno-chromatography directly from whole blood). The details for implementing the experiments are explained below. Under A, as a process according to the invention, immune transfer is described with co-associated analyte detection by means of TRACE technology; under B, as a process according to the invention, immune transfer with associated analyte detection by means of immunochromatography is described; under C, the standard immunochromatography is described as a reference method. A comparison of the precision profiles of the variants A, B and C is depicted in FIG. 2.

A. Immune Extraction of PCT from Whole Blood and Analyte Detection by Means of TRACE Technology As a solid phase, microtiter plates that consist of high-binding polystyrene were used, which were coated with oligo-Lys-BSA, by which a first anti-PCT antibody was bonded, which had been derivatized in advance with oligo-Asp and cryptate. A PCT-containing whole-blood sample was then briefly incubated, and PCT was immune-extracted from the sample in the solid phase. After the solid phase was washed, dissolution buffer was added and shortly incubated. An aliquot was conveyed into another, low-binding black microtiter plate and mixed with a solution that contained a second cyanin-labeled anti-PCT antibody. After a short incubation, the sandwich formation was detected after excitation with laser light by means of TRACE technology.

In particular, the test was performed as follows:

A.1. Production of the Conjugates for the Solid Phase

A.1.1. Production of BSA+Oligo-Lys Conjugate: See Above

A.1.2. Production of Anti-Calcitonin Sheep Antibody Cryptate MonoMP+Oligo-Asp Conjugate For the labeling with the cryptate monophosphate ("KMonoMP," Cezanne Company, Nimes, France), a polyclonal anti-calcitonin sheep antibody ("anti-PCT antibody 1") was activated with SPDP (N-succinimidyl 3-(2-pyridyldithio)propionate, Pierce Company, Rockford, Ill., USA, Art. No. 21857) at a molar ratio 1:4 (see "SPDP Reagents Instructions," Pierce, Rockford, Ill., USA).

5 mg of antibody (dissolved in 1.5 ml of 100 mM sodium phosphate, 5 mM EDTA, pH 6.9) was mixed with 41.6 µl of 3.2 mM SPDP (freshly dissolved in ethanol) and incubated for 30 minutes at room temperature.

The activated antibody was reduced with 81.2 µl of 200 mM DTT (dithiothreitol, dissolved in 100 mM sodium phosphate, 5 mM EDTA, pH 6.9) for 15 minutes at room temperature.

The product was purified on two NAP10 columns (mobile solvent: 100 mM sodium phosphate, 5 mM EDTA, pH 6.9), and the protein content was determined by photometry.

Then, the conjugation of the eluate was carried out immediately with freeze-dried KMonoMP at a molar ratio 1:8. After incubation for 20 hours at 4° C., the product was purified once more on three NAP10 columns (mobile solvent: PBS, 10 mM EDTA, pH 8), and the protein content was determined by photometry.

For coupling the oligo-Asp peptide "D14C" (amino acid sequence DDDDDDDDDDDDDDC, (SEQ ID NO. 2), JPT Company GmbH, Berlin, Germany, M=1731.43), the product was activated with SMCC at the ratio 1:25 (see "SMCC and Sulfo-SMCC Instructions," Pierce, Rockford, Ill., USA): 3 mg of product (eluted with 4.5 ml of PBS, 10 mM EDTA, pH 8) was mixed with 5.0 µl of 100 mM SMCC (freshly dissolved in DMSO) and incubated for 30 minutes at room temperature. The product was purified on two NAP25 columns (mobile solvent: PBS, 10 mM EDTA, pH 8), and the protein content was determined by photometry.

Then, the conjugation was carried out immediately with the oligo-Asp peptide (dissolved in distilled water) at a molar ratio 1:100. After incubation for 60 minutes at room temperature, the reaction was stopped with 100 µl of 100 mM cysteine for 10 minutes, non-conjugated peptide was separated on NAP25 columns (mobile solvent: PBS, pH 7.4), and the protein content was determined by photometry.

The anti-calcitonin sheep antibody-K monoMP+oligo-Asp conjugate was stored aliquoted at −20° C.

A.2. Coupling of the Conjugates to Microtiter Plates

A.2.1. Coupling: BSA+Oligo-Lys Conjugate

Irradiated microtiter plates (Greiner Company, Frickenhausen, Germany) were coated with BSA-oligo-Lys conjugate as follows:

The conjugate was diluted with a solution of 10 mM Tris, 100 mM NaCl, pH 7.8 to a concentration of 6.67 µg/ml. 300 µl of this solution was pipetted into each cavity and incubated for 20 hours at 22° C. The solution was suctioned off. Then, each cavity was saturated with 300 µl of 0.5% bovine serum albumin, 2% Karion FP for 2 hours, and once more suctioned off. Then, the binding of the anti-calcitonin sheep antibody-cryptate monoMP+oligo-Asp conjugate was carried out.

A.2.2. Bond: Anti-Calcitonin Sheep Antibody Cryptate MonoMP+Oligo-Asp Conjugate

The conjugate was diluted in PBS, 0.5% protease-free BSA, pH 7.4 to a concentration of 667 ng/ml. 300 µl of this solution was pipetted into each cavity and incubated for 1 hour at 22° C. The solution was suctioned off. Then, each cavity was saturated with 300 µl of 0.5% bovine serum albumin, 2% Karion FP for 2 hours, and once more suctioned off.

Then, the microtiter plates were dried in a vacuum dryer and stored at 4° C.

A.3. Production of an Anti-Catacalcin Mouse Antibody-Cy5 Conjugate for the Liquid Phase A monoclonal anti-catacalcin antibody ("anti-PCT antibody 2") was labeled in the presence of 45% (2-hydroxyl-propyl)-β-cyclodextrin (Aldrich Company, Seelze, Germany, Art. No. 33,260-7) with Cy5-NHC (Amersham Company, Art. No. PA15100) at a molar ratio 1:20 (see Product Booklet "Amersham CyDye Mono-Reactive NHS Esters").

213 µl of antibody (c=10 mg/ml in PBS, pH 7.4) was mixed with 750 µl of 60% cyclodextrin (dissolved in 100 mM carbonate buffer, pH 9) and mixed with 37.3 µl of 7.7 mM Cy5-NHS (dissolved in DMSO). After incubation for one hour at room temperature, the batch was stopped for 10 minutes with 50 µl of 50 mM glycine and prepurified on an NAP10 column (mobile solvent PBS, pH 7.4).

For separation of the last Cy5-NHS radicals that are not bonded to antibodies, a gel filtration-HPLC was performed (column: Bio-Sil Sec 125, Biorad Company, Munich, Germany). The sample was applied and chromatographed at a flow rate of 1 ml/minute with PBS, pH 7.4. The wavelengths 280 nm and 648 nm were measured with a flow photometer. The absorption ratio of 648 nm/280 nm as a measurement for the degree of labeling of the antibody was 1.48 at the peak. The antibody-containing fractions (retention time 8-10 minutes) were pooled.

The anti-catacalcin mouse antibody-Cy5 conjugate was stored in portions at −20° C.

A.4. Immune Transfer and TRACE Assay

The assay that is decribed below was performed for each sample in 10× determination. In the cavities of the microtiter plates that were coated with BSA+oligo-Lys and anti-calcitonin sheep antibody cryptate MonoMP+D14C conjugate, 300 μl of EDTA-whole-blood samples, stocked up with recombinant PCT (InVivo Gmbh, Hennigsdorf, Germany), was pipetted and incubated for 15 minutes at room temperature (the PCT concentrations of the samples were determined from plasma by measuring with the LIA-sensitive BRAHMS PCT assay (BRAHMS AG, Hennigsdorf, Germany)). Then, it was washed 2× with 300 μl of PBS, pH 7.4, and then 2× with 300 μl of washing solution (8 mM Tris, 60 mM NaCl, 0.2% Tween 20, pH 7.5). Then, it was incubated for 10 minutes with 300 μl of dissolution buffer (PBS, pH 7.4, 0.6M KF, 0.5% BSA, 0.01% heparin). From the dissolved immune complex, 100 μl was conveyed in microtiter plates suitable for the TRACE measurement (Costar Half Area Plates, 96-well, black, polystyrene, Sigma/Aldrich Company, Seelze, Germany, Catalyst. No. CLS 3694-100EA) and incubated for 19 minutes at room temperature with 50 μl of anti-catacalcin mouse antibody-Cy5-NHS conjugate (c=20 μg/ml in PBS, pH 7.4, 0.6 M KF, 0.5% BSA, 0.01% heparin). The measurement of the TRACE signals (620 nm and 665 nm) was carried out by means of the High-Performance Time-Resolved Fluorescence Microtiter Plate Reader RUBYstar (BMG LABTECH Company GmbH, Offenburg, Germany).

The following device settings were made in this case on the RUBYstar:

| | |
|---|---|
| Number of flashes | 20 |
| Integration delay [μs] | 50 |
| Integration time [μs] | 400 |
| Interval time [μs] | 10 |
| Number of intervals | 45 |
| Ratio Multiplicator | 10,000 |

For each sample, the following was calculated from the ratio $OD_{665\ nm}/OD_{620\ nm}$ Delta F:

$$\text{Delta } F = (\text{Ratio}_{pos} - \text{Ratio}_{neg})/\text{Ratio}_{neg}$$

In this case, $\text{ratio}_{neg}$ means the ratio of a PCT-negative sample (i.e., sample that does not contain or cannot detect PCT), and $\text{ratio}_{pos}$ means the ratio of a sample that is to be tested (i.e., a potential PCT-containing sample). The respective mean value was derived from the 10× determinations of the individual samples. These values are used as standard concentrations, on which the concentrations of all individual samples were determined with use of the MultiCalc (Spline Fit) software. The variation coefficient was determined for each 10× determination.

B. Immune Extraction of PCT from Whole Blood and Analyte Detection by Means of Immunochromatogrphy As a solid phase, polystyrene tubes were used that were coated with oligo-Lys-BSA, to which a first anti-PCT antibody was bonded, which had been derivatized in advance with oligo-Asp and biotin. A PCT-containing whole-blood sample was then briefly incubated, and in this case, PCT was immune-extracted from the sample in the solid phase. After the solid phase was washed, dissolution buffer was added, which contained a second anti-PCT antibody that was labeled with colloidal gold, and briefly incubated. The solution was finally immunochromatographed on a test strip, on which streptavidin was sprayed as a test band. The biotinylated first anti-PCT antibody and thus PCT also bonded thereto and the in turn second gold-labeled anti-PCT antibody bonded thereto bind to the streptavidin. The detection of the label was carried out by reflectometry.

In particular, the test was performed as follows:

B.1. Production of the Conjugates for the Solid Phase

B.1.1. Production of the BSA+Oligo-Lys Conjugate: See Above

B.1.2. Production of Anti-Calcitonin Sheep Antibody Biotinylated+Oligo-Asp Conjugate A polyclonal anti-calcitonin sheep antibody ("anti-PCT antibody 1") was mixed with EZ-link sulfo-NHS-LC-LC-biotin (Pierce Company, Rockford, Ill., USA, Art. No. 21338) at a molar ratio 1:10 (see "EZ-Link Sulfo-NHS-LC-LC-Biotin Instructions," Pierce, Rockford, Ill., USA): 1.6 mg of antibody (in PBS, pH 7.4) was mixed with 10 μl of 10 mM EZ-link sulfo-NHS-LC-LC-biotin (freshly dissolved in distilled water) and incubated for 30 minutes at room temperature.

The product was purified on an NAP5 column (mobile solvent: PBS, 10 mM EDTA, pH 8.0), and the protein content was determined by photometry.

For coupling the oligo-Asp peptide "D14C" (amino acid sequence DDDDDDDDDDDDDDC, (SEQ ID NO. 2)), (JPT Company GmbH, Berlin, Germany, M=1731.43), the product was activated with SMCC at the ratio 1:50 (see "SMCC and Sulfo-SMCC Instructions," Pierce, Rockford, Ill., USA).

1.3 mg of product (eluted with 1.0 ml of PBS, 10 mmol of EDTA, pH 8) was mixed with 4.33 μl of 100 mM SMCC (freshly dissolved in DMSO) and incubated for 30 minutes at room temperature. The product was purified on an NAP10 column (mobile solvent: PBS, 10 mmol of EDTA, pH 8), and the protein content was determined by photometry.

Then, the conjugation was carried out immediately with the oligo-Asp peptide (dissolved in distilled water) at a molar ratio 1:100. After incubation for 60 minutes at room temperature, the reaction was stopped for 10 minutes with 100 μl of 100 mM cysteine, non-conjugated peptide was separated on an NAP25 column (mobile solvent: PBS, pH 7.4), and the protein content was determined by photometry.

The anti-calcitonin sheep antibody biotinylated+oligo-Asp conjugate was stored aliquoted at −20° C.

B.2. Coupling of the Conjugate to the Tubes

B.2.1. Coupling: BSA+Oligo-Lys Conjugate

Irradiated star tubes (Greiner Company, Frickenhausen, Germany) were coated with BSA-oligo-Lys conjugate as follows:

The conjugate was diluted with a solution of 10 mM Tris, 100 mmol of NaCl, pH 7.8 to a concentration of 6.67 μg/ml. 300 μl of this solution was pipetted into each tube and incubated for 20 hours at 22° C. The solution was suctioned off. Then, each tube was saturated with 300 μl of 0.5% bovine serum albumin, 2% Karion FP for 2 hours and suctioned off once more. Then, the binding of the anti-calcitonin sheep antibody biotinylated+oligo-Asp conjugate was carried out.

B.2.2. Bond: Anti-Calcitonin Sheep Antibody Biotinylated+ Oligo-Asp Conjugate

The conjugate was diluted in PBS, 0.5% protease-free BSA, pH 7.4 to a concentration of 667 ng/ml. 300 μl of this solution was pipetted into each tube and incubated for 1 hour at 22° C. The solution was suctioned off. Then, each tube was saturated once more with 300 μl of 0.5% bovine serum albumin, 2% Karion FP for 2 hours and then suctioned off.

Then, the tubes were dried in a vacuum dryer and stored at 4° C.

B.3. Production of Gold-Labeled Anti-Catacalcin Antibody:

This component was bought from the 8sens.biognostic Company GmbH, Berlin, Germany. The monoclonal anticatacalcinin antibody was coupled to colloidal gold (8sens. biognostic Company GmbH, Berlin, Germany; according to Frens: Frens, G., Nature Physical Science, 1973, 241 20-22) as described in Hermanson (http://www.amazon.de/Bioconjugate-Techniques-Greg-T-Hermanson/dp/0123423368).

B.4. Production of Test Strips:

This component was bought from the 8sens.biognostic Company GmbH, Berlin, Germany. Nitrocellulose membranes of MDI (Advanced Microdevices, Ambala, India) were coated with 4 µg/cm of streptavidin (Pierce, Rockford, Ill., USA) (test line) as well as with 2.5 µg/cm of anti-mouse IgG antibody (Scantibodies, Santee, Calif., USA) (control line). A microdispenser of the Biodot Company, Irvine, Calif., USA was used to apply the trap molecule. Then, the drying of the membrane was carried out overnight at 50° C. AP22 of the Millipore Company, Billerica, Mass., USA was used as a suction pad.

B.5. Immune Transfer and Immunochromatography:

The assay that is described below was performed for every sample in 10× determination. In the tube coated with BSA+oligo-Lys and anti-calcitonin sheep antibody biotinylated+D14C conjugate, 300 µl of EDTA-whole-blood samples, stocked up with recombinant PCT (InVivo GmbH, Hennigsdorf, Germany), was pipetted and incubated for 15 minutes at room temperature (the PCT concentrations of the samples were determined from plasma by measuring with the LIA-sensitive BRAHMS PCT assay (BRAHMS AG, Hennigsdorf, Germany). Then, it was washed 2× with 300 µl of PBS, pH 7.4, and then 2× with 300 µl of washing solution (8 mM Tris, 60 mM NaCl, 0.2% Tween 20, pH 7.5). Then, it was incubated with 150 µl of dissolution buffer (PBS pH 7.4, 5% BSA, 0.5% Tween 20, 0.01% heparin), which also contained the gold-labeled anti-catacalcin monoclonal antibody, while being shaken for 10 minutes. 150 µl in cavities of low-binding microtiter plates was moved from the dissolved immune complex. Then, the immunochromatography was carried out directly with the test strips by the latter being inserted into the cavities. After 30 minutes, the coloring of the test band was determined with a reflectometer from the LRE Medical Company GmbH, Munich, Germany.

The respective mean value was derived from the 10× determinations of the individual samples. The values were used as standard concentrations, on which the concentrations of all individual samples were determined with use of the Multi-Calc (Spline Fit) software. The coefficient of variation was determined at each 10× determination.

C. Detection of PCT from Whole Blood by Means of Standard Immunochromatography

Test strips were produced that were provided on the sample application zone with a membrane that was suitable for retaining blood cells from a whole-blood sample to be applied. A porous cushion ("sample pad"), which in the dried state contained, on the one hand, a first biotinylated anti-PCT antibody, and, on the other hand, a second colloidal-gold-labeled anti-PCT antibody, was attached between this membrane and the test strip. As a test band, streptavidin was sprayed onto the strips. The test strips were inserted in plastic cassettes. A PCT-containing whole-blood sample was immunochromatographed. The biotinylated first anti-PCT antibody and thus also the PCT bonded thereto and in turn the second, gold-labeled anti-PCT antibody bonded thereto bind to the streptavidin. The detection of the label was carried out by reflectometry.

In particular, the test was performed as follows:

C.1. Production of the Conjugates for the Solid Phase

C.1.1. Production of the BSA+Oligo-Lys Conjugate: See Above

C.1.2. Production of Anti-Calcitonin Sheep Antibody Biotinylated+Oligo-Asp Conjugate: See Above C.2. Production of Gold-Labeled Anti-Catacalcin Antibody: See Above C.3. Production of Test Strips:

This component was bought from the 8sens.biognostic Company GmbH, Berlin, Germany. Nitrocellulose membranes of MDI (Advanced Microdevices, Ambala, India) were coated with 4 µg/cm of streptavidin (Pierce, Rockford, Ill., USA) (test line) as well as with 2.5 µg/cm of anti-mouse IgG antibody (Scantibodies, Santee, Calif., USA) (control line). A microdispenser of the Biodot Company, Irvine, Calif., USA was used to apply the trap molecule. Then, the drying of the membrane was carried out overnight at 50° C. AP22 of the Millipore Company, Billerica, Mass., USA was used as a suction pad. For the production of the whole-blood tests, a whole-blood setup of the 8sens.biognostic Company was used. In the sample application area, on the one hand, the anti-catacalcin antibody that is coupled to colloidal gold and, on the other hand, the biotinylated+oligo-Asp-derivatized anti-calcitonin antibody were immobilized on 2 separate pads. A standard housing of the 8sens.biognostic Company was used as a cassette.

C.4. Standard Immunochromatography

The immunochromatography that is described below was performed for each sample in 10× determination. 120 µl of EDTA-whole-blood samples, stocked up with recombinant PCT (InVivo GmbH, Hennigsdorf, Germany), was pipetted onto the test strips (the PCT concentrations of samples were determined from plasma by measurement with the LIA-sensitive BRAHMS PCT assay (BRAHMS AG, Hennigsdorf, Germany)). After 30 minutes, the coloring of the test band was determined with a reflectometer from the LRE Medical Company GmbH, Munich, Germany.

The respective mean value was derived from the 10× determinations of the individual samples. These values were used as standard concentrations, on which the concentrations of all individual samples were determined with use of the Multi-Calc (Spline Fit) software. The coefficient of variation was determined for each 10× determination.

D. Immune Extraction of MR-proADM from Whole Blood and Analyte Detection by Means of Immunochromatography As another example for the process of immune extraction from whole blood and analyte detection by means of immunochromatography, a test system was developed for the MR-proADM analytes (mid-regional pro-adrenomedullin). MR-proADM is a stable peptide that circulates in the blood and that is known from the proteolytic processing of the precursor of adrenomedullin (Struck, J. et al: Peptides, 2004 August; 25 (8): 1369-72). Adrenomedullin is one of the best known endogenic vasodilators, which is involved in the regulation of numerous biological processes, in particular in the regulation of the cardiovascular system (Beltowski, J. et al.: Pol J Pharmacol. 2004 January-February; 56 (1): 5-27). The measurement of MR-proADM has proven useful as a surrogate marker for the mature adrenomedullin that cannot be measured reliably within the framework of diagnosis and prognosis of various disease conditions. These include, i.a.: COPD (Stolz, D. et al.: Chest. 2008 May 19 [Epub ahead of print]), Pneumonia (Christ-Cain, M. et al.: Crit Care. 206; 10 (3): R96.), Sepsis (Christ-Crain, M. et al.: Crit Care. 2005; 9 (6): R816-24.), Myocardial Infarction (Khan, S. Q. et al.: J Am Coll Cardiol. 2007 Apr. 10; 49 (14): 1525-32.), Heart Failure (Gegenhuber, A. et al.: J Card Fail. 2007 February; 13 (1): 42-9.).

For MR-proADM, the process according to the invention shows a high precision both in the normal range (Morgenthaler, N. G. et al.: Clin Chem. 2005 October; 51(10): 1823-9) and in the area of elevated concentrations, which are associated with various clinical pictures (see above) (FIG. 3).

In particular, the test was performed as follows:

D.1. Production of Conjugates for the Solid Phase

D.1.1. Production of BSA+Oligo-Lys Conjugate: See Above

D.1.2. Production of Anti-"SPCD19" Sheep Antibody Biotinylated+Oligo-Asp Conjugate For coupling the oligo-Asp peptide "D14C" (amino acid sequence DDDDDDDDDDDDDDC, (SEQ ID NO. 2), JPT Company GmbH, Berlin, Germany, M=1731.43), a polyclonal anti-"SPCD19" (amino acid sequence CRPQDMKGASRSPEDSSPD, (SEQ ID NO. 10) of the JPT Company GmbH, Berlin, Germany, M=2063) sheep antibody was activated with SMCC at a ratio 1:25 (see "SMCC and Sulfo-SMCC Instructions," Pierce, Rockford, Ill., USA).

1.0 mg of antibody was mixed with 16.67 µl of 10 mM SMCC (freshly dissolved in DMSO) and 103 µl of PBS, 10 mM EDTA, pH 8, and it was incubated for 30 minutes at room temperature. The product was purified on an NAP5 column (mobile solvent: PBS, 10 mM EDTA, pH 8), and the protein content was determined by photometry.

Then, the conjugation with the oligo-Asp peptide (dissolved in distilled water) was carried out immediately at a molar ratio 1:100. After incubation for 60 minutes at room temperature, non-conjugated peptide was separated on an NAP10 column (mobile solvent: PBS, pH 7.4), and the protein content was determined by photometry.

The product was mixed with EZ-link sulfo-NHS-LC-LC-biotin (Pierce Company, Rockford, Ill., USA, Art. No. 21338) at a molar ratio of 1:20 (see "EZ-Link Sulfo-NHS-LC-LC-Biotin Instructions," Pierce, Rockford, Ill., USA): 900 µg of antibody (in PBS, pH 7.4) was mixed with 12 µl of 10 mM EZ-link sulfo-NHS-LC-LC-biotin (freshly dissolved in distilled water). After incubation for 30 minutes at room temperature, the reaction was stopped for 10 minutes with 50 µl of 1 M Tris. The product was purified on an NAP25 column (mobile solvent: PBS, pH 7.4), and the protein content was determined by photometry.

The anti-"SPCD19" sheep antibody biotinylated+oligo-Asp conjugate was stored aliquoted at −20° C.

D.2. Coupling of the Conjugate to the Tubes

D.2.1. Coupling: BSA+Oligo-Lys Conjugate

Irradiation star tubes (Greiner Company, Frickenhausen, Germany) were coated with BSA-oligo-Lys conjugate as follows:

The conjugate was diluted with a solution of 10 mM Tris, 100 mM NaCl, pH 7.8 to a concentration of 6.67 µg/ml. 300 µl of this solution was pipetted into each tube and incubated for 20 hours at 22° C. The solution was suctioned off. Then, each tube was saturated with 300 µl of 0.5% bovine serum albumin, 2% Karion FP for 2 hours, and suctioned off once more. Then, the binding of the anti-calcitonin sheep antibody biotinylated+oligo-Asp conjugate was carried out:

D.2.2. Bond: Anti-"SPCD19" Sheep Antibody Biotinylated+Oligo-Asp Conjugate

The conjugate was diluted in PBS, 0.5% protease-free BSA, pH 7.4, to a concentration of 667 ng/ml. In each tube, 300 µl of this solution was pipetted and incubated for 1 hour at 22° C. The solution was suctioned off. Then, each tube was saturated once more with 300 µl of 0.5% bovine serum albumin, 2% Karion FP, for 2 hours and then suctioned off.

Then, the tubes were dried in a vacuum dryer and stored at 4° C.

D.3. Production of Gold-Labeled Anti-"PSV11" Antibodies:

A monoclonal anti-"PSV11" antibody was used (PSV11 represents a partial sequence of MR-proADM; amino acid sequence CSSPDAARIRV, (SEQ ID NO. 11), JPT Company GmbH, Berlin, Germany, M=1174). The antibody was coupled to colloidal gold (BBI International Company, EM.GC 60 nm) as described by Hermanson.

D.4. Production of the Test Strips:

This component was bought from 8sens.biognostic GmbH, Berlin, Germany. Nitrocellulose membranes from MDI (Advanced Microdevices, Ambala, India) were coated with 4 µg/cm of strepatavidin (Pierce, Rockford, Ill., USA (test line). A microdispenser from the Biodot Company, Irvine, Calif., USA was used to apply the trap molecule. Then, the drying of the membrane overnight at 50° C. was carried out. AP22 of the Millipore Company, Billerica, Mass., USA was used as a suction pad.

D.5. Immune Transfer and Immunochromatography:

The assay described below was performed for each sample in a 10× determination. 300 µl of EDTA-whole-blood samples, stocked up with synthetic 45-92 pro-adrenomedullin (amino acid sequence ELRMSSSYPTGLADVKAG-PAQTLIRPQDMKGASRSPEDSSPDAARIRV (SEQ ID NO. 9) JPT Company GmbH, Berlin, Germany, M=5115), was pipetted into the tube coated with BSA+oligo-Lys and anti-"SPCD19" sheep antibody biotinylated+"D14C" conjugate, and incubated for 15 minutes at room temperature (the proADM concentrations of samples were determined from plasma by measuring with the proADM LIA BRAHMS assay (BRAHMS AG, Hennigsdorf, Germany). Then, it was washed 5× with 1 ml of washing solution (8 mM Tris, 60 mM NaCl, 0.2% Tween 20, pH 7.5).

Then, while being shaken for 10 minutes, it was incubated with 150 µl of dissolution buffer (PBS, pH 7.8, 0.5% BSA, 0.1% Tween 20, 0.1% heparin, 0.08% NaN$_3$), which also contained the gold-labeled anti-"PSV11" monoclonal antibody. From the dissolved immune complex, 100 µl was moved into cavities from low-binding microtiter plates. Then, the immunochromatography was carried out directly with the test strips, by the latter being inserted into cavities. After 30 minutes, the coloring of the test band was determined with a reflectometer from the LRE Medical Company GmbH, Munich, Germany.

The respective mean value was derived from the 10× determinations of the individual samples. These values were used as standard concentrations, on which the concentrations of all individual samples were determined with use of the MultiCalc (Spline Fit) software. The coefficient of variation was determined for each 10× determination.

Figure 1:
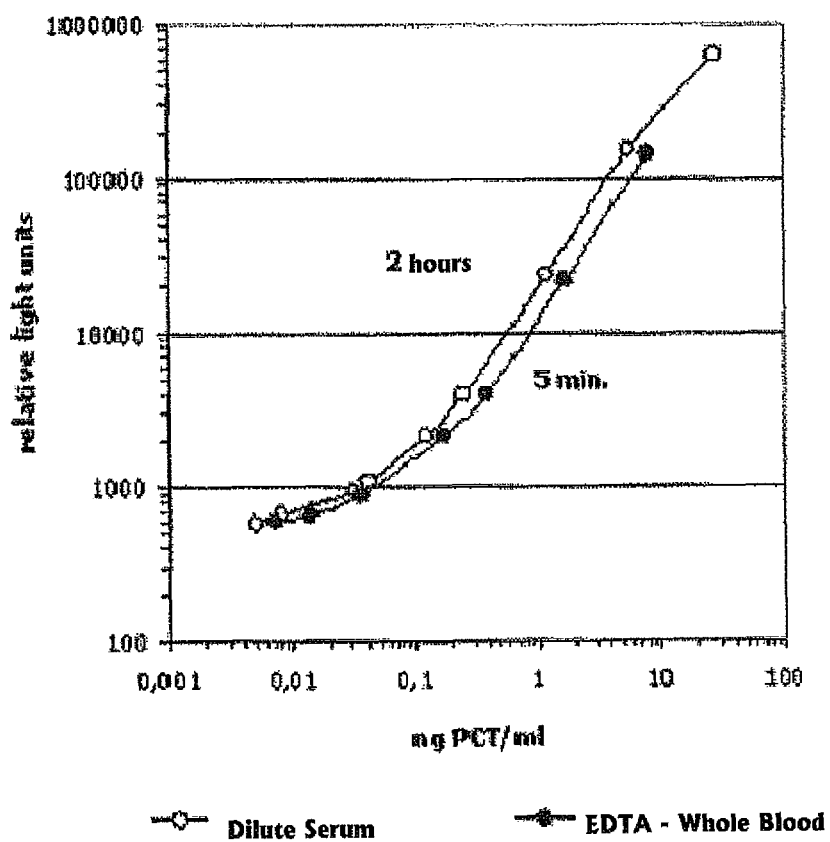
FIG. 1 shows that the analyte (PCT) can be immune-extracted from whole blood, specifically as early as after only 5 minutes of incubation with similar efficiency to the reference method after 2 hours of incubation.
Figure 2:
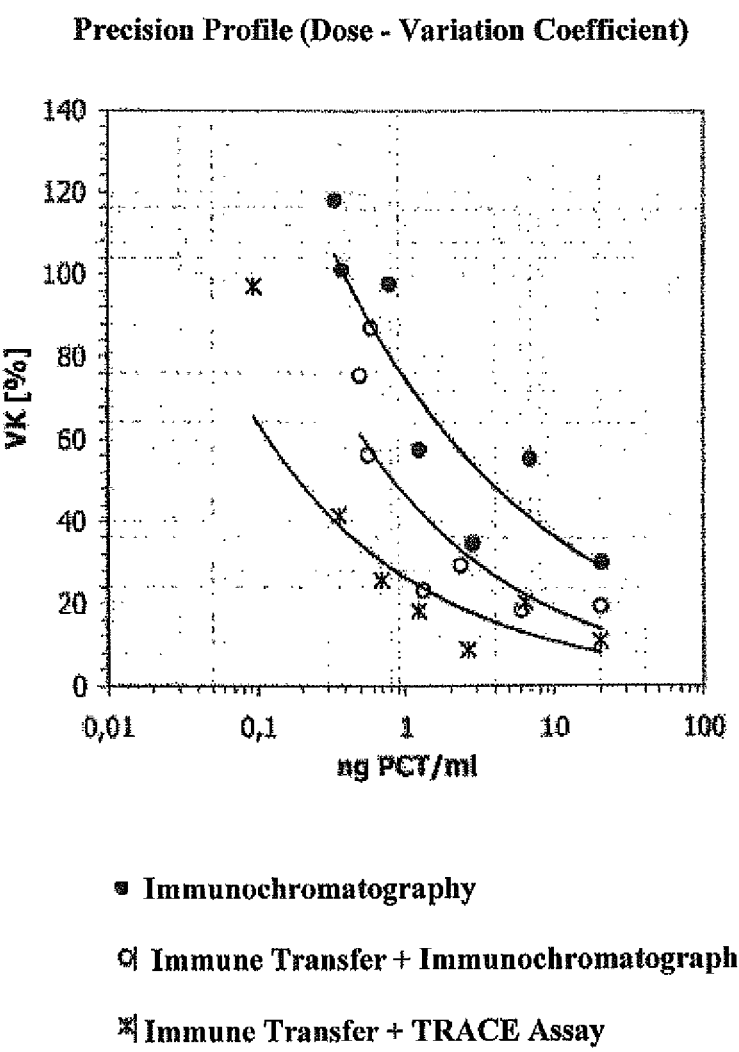
FIG. 2: The coefficient of variation for the multiple determinations of whole-blood samples with various PCT concentrations are shown, as they were determined with the following three indicated methods (A: immune transfer with TRACE technology, B: immune transfer with immunochromatography, C: reference of standard immunochromatography). Both processes that contain immune transfer represent processes according to the invention; the standard immunochromatography is the reference process.
Figure 3:
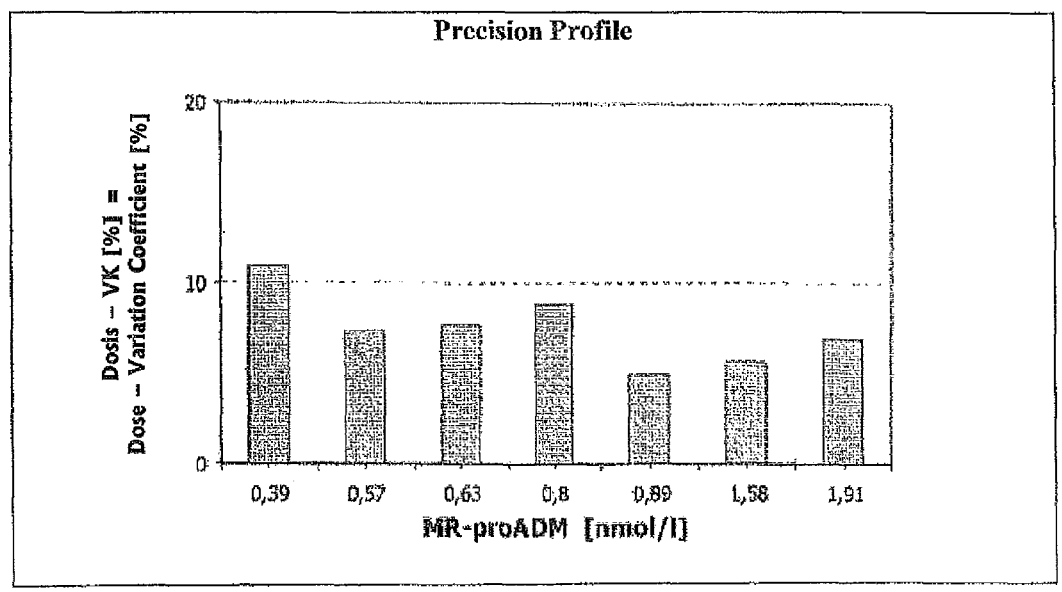
FIG. 3: The coefficient of variations for the multiple determinations of whole-blood samples with various MR-proADM concentrations are shown, as they were determined with the method according to the invention of immune transfer with immunochromatography.

Bibliography (1)
M. J. Pugia, C. P. Price: Point-of-Care Testing, 2$^{nd}$ Ed., edited by Price, John, Hicks, American Association for Clinical Chemistry, ISBN 1-59425-012-X, 2004; pages 13-30

(2)
Saadeddin, S. et al.: Reliability of the Rapid Bedside Whole-Blood Quantitative Cardiac Troponin T Assay in the Diagnosis of Myocardial Injury in Patients with Acute Coronary Syndrome, Med Sci Monit. 2004 March; 10(3): MT43-6. Epub 2004 Mar. 1

(3)
o.V.—Evaluation of a Bedside Whole-Blood Rapid Troponin T Assay in the Emergency Department. Rapid Evaluation by Assay of Cardiac Troponin T (REACTT) Investigators Study Group, Acad Emerg Med. 1997 November; 4(11): 1018-24

(4)
Zugck, C. et al.: Multicenter Evaluation of a New Point-of-Care Test for the Determination of NT-proBNP in Whole Blood, Clin Chem Lab Med. 2006; 44(10): 1269-77

(5)
Alan, H. B.: A Platform for Quantitative Point-of-Care Cardiac Marker Determinations from Roche Diagnostics (6)
Yeo, K. T. et al.: Multicenter Evaluation of the Roche NT-proBNP Assay and Comparison to the Biosite Triage BNP Assay, Clin Chim Acta. 2003 December: 338 (1-2): 107-15

(7)
Meisner, M. et al.: Clinical Experiences with a New Semi-Quantitative Solid-Phase Immunoassay for Rapid Measurement of Procalcitonin, Clin Chem Lab Med. 2000 October; 38 (10): 989-95

(8)
Terpe, K.: Overview of Tag Protein Fusions: From Molecular and Biochemical Fundamentals to Commercial Systems, Appl Microbiol Biotechnol. 2003 January; 60(5): 523-33. Epub 2002 Nov. 7

(9)
R. C. Stevens: Fusion Tags Used in Recombinant Protein Expression and Purification—Design of High-Throughput Methods of Protein Production for Structural Biology, Structure, 8, R177-R185 (2000).

(10)
Stevens, R. C.: Design of High-Throughput Methods of Protein Production for Structural Biology Structure. 2000 Sep. 15; 8(9): R177-85

(11)
Hopp, T. P., Gallis, B., Prickett, K. S.: Metal-Binding Properties of a Calcium-Dependent Monoclonal Antibody, Mol Immunol. 1996 May-June; 33 (7-8): 601-8

(12)
Stearns, D. J. et al.: The Interaction of a Ca2+-Dependent Monoclonal Antibody with the Protein C Activation Peptide Region. Evidence for Obligatory Ca2+ Binding to Both Antigen and Antibody, J Biol Chem. 1988 Jan. 15; 263 (2): 826-32

(13)
QIAexpress Detection and Assay Handbook October/2002, QIAGEN, HILDEN, GERMANY

(14)
Sassenfeld, H. M. and Brewer, S. J. (1984) *Bio/Technology*, 2, 76-80.

(15)
Dalboge, H., Dahl, H.-H. M., Pedersen, J., Hansen, J. W., and Christensen, T. (1987), *Bio/Technology*, 5, 161-164

(16)
Zhao, J. Y., Ford, C. F., Glatz, C. E., Rougvie, M. A., and Gendel, S. M. (1990), *J. Biotechnol.*, 14, 273-283

(17)
Avidin-Biotin Chemistry: A Handbook

(18)
Invitrogen (Library)

(19)
Pierce: Immobilized Monomeric Avidin Kit, piercenet.com

(20)
Pierce: Two Thiol Cleavable, Heterobifunctional, Amine- and Sulfhydryl-Reactive Crosslinking Agents, pierenet.com

(21)
Meisner, M.: Pathobiochemistry and Clinical Use of Procalcitonin, Clin Chim Acta. 2002 September; 323 (1-2): 17-29

(22)
Meisner, M. et al.: Clinical Experiences with a New Semi-Quantitative Solid Phase Immunoassay for Rapid Measurement of Procalcitonin, Clin Chem Lab Med. 2000 October; 38 (10): 989-95

(23)
Morgenthaler, N. G. et al.: Sensitive Immunoluminometric Assay for the Detection of Procalcitonin, Clin Chem. 2002 May; 48 (5): 788-90

The invention claimed is:

1. A method for detection of an analyte from a biological sample, comprising:
   a) contacting the biological sample with a reversible binding partner 1 immobilized on a solid phase, to which a first analyte binder is reversibly bound via a reversible binding partner 2, that is itself bound to the first analyte binder, whereby the first analyte binder is immobilized by way of the bond between the reversible binding partners 1 and 2,
      wherein the binding pair of reversible binding partners 1 and 2 is selected from one of the following binding pairs:
      i. positively- and negatively-charged peptide oligomers,
      ii. $Ca^{2+}$-binding peptide/protein and antibodies that the peptide/protein binds with high affinity, when the peptide/protein has bonded $Ca^{2+}$,
      iii. an oligohistidine and Ni—NTA,
      wherein the first analyte binder is labeled, and
      whereby the analyte is bound to the reversibly immobilized first analyte binder when the biological sample contains the analyte,
   b) separating the biological sample,
   c) adding a dissolution buffer, which breaks the bond between the reversible binding partners 1 and 2, whereby the binding of the analyte to the first analyte binder remains optional, and wherein the dissolution buffer further contains a second analyte binder labeled for detection in a sandwich immunoassay, whereby the first analyte binder is labeled and remains labeled with a label for the detection of analytes after the dissolution buffer is added, and
   d) detecting the analyte in the dissolution buffer in the case that the biological sample contains the analytes, and/or determining the absence of the analyte in the case that the biological sample does not contain the analytes, respectively.

2. The method of claim 1, whereby the biological fluid is an unprocessed whole-blood sample.

3. The method of claim 1, whereby the immobilized reversible binding partner 1 is immobilized directly or by means of a carrier protein.

4. The method of claim 1, whereby the first analyte binder is bonded covalently to the reversible binding partner 2.

5. The method of claim 1, whereby the first analyte binder is an anti-procalcitonin (anti-PCT) antibody.

6. The method of claim 1, whereby the $Ca^{2+}$-binding peptide/protein is a FLAG peptide and the antibody is an M1 antibody, or the $Ca^{2+}$-binding peptide/protein is a protein C peptide, and the antibody is an HPC4 antibody.

7. The method of claim 1, whereby the detection of the labeled analyte is carried out by an immunoassay with use of TRACE technology.

8. The method of claim 1, whereby the detection of the labeled analyte is carried out by means of immunochromatography.

9. The method of claim 1, whereby the biological sample is used undiluted and in such a volume that the coated portion of the solid phase is brought completely into contact with the biological sample.

10. The method of claim 1, whereby the period of adding the sample until detection does not exceed 30 minutes, and the method can be regarded as a quick-test method.

11. The method of claim 1, wherein the oligohistidine is 6His.

* * * * *

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of artificial sequence: His-
      tag peptide PRG12"

<400> SEQUENCE: 1

Arg Gly Ser His His His His His His Gly Gly Cys
1               5                   10
```

```
<210> SEQ ID NO 2
<211> LENGTH: 15
<212> TYPE: PRT
<213> ORGANISM: Artificial Sequence
<220> FEATURE:
<221> NAME/KEY: source
<223> OTHER INFORMATION: /note="Description of artificial sequence:
      Oligo-Asp peptide D14C"

<400> SEQUENCE: 2

Asp Asp Asp Asp Asp Asp Asp Asp Asp Asp Asp Asp Asp Asp Cys
1               5                   10                  15

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of artificial sequence:
      Flag-tag peptide PDC12"

<400> SEQUENCE: 3

Asp Tyr Lys Asp Asp Asp Asp Lys Gly Gly Gly Cys
1               5                   10

<210> SEQ ID NO 4
<211> LENGTH: 15
<212> TYPE: PRT
<213> ORGANISM: Artificial Sequence
<220> FEATURE:
<221> NAME/KEY: source
<223> OTHER INFORMATION: /note="Description of artificial sequence:
      ProtC-tag peptide PEG15"

<400> SEQUENCE: 4

Glu Asp Gln Val Asp Pro Arg Leu Ile Asp Gly Lys Gly Gly Cys
1               5                   10                  15

<210> SEQ ID NO 5
<211> LENGTH: 15
<212> TYPE: PRT
<213> ORGANISM: Artificial Sequence
<220> FEATURE:
<221> NAME/KEY: source
<223> OTHER INFORMATION: /note="Description of artificial sequence:
      Oligo-Lys peptide K14C"

<400> SEQUENCE: 5

Lys Lys Lys Lys Lys Lys Lys Lys Lys Lys Lys Lys Lys Lys Cys
1               5                   10                  15

<210> SEQ ID NO 6
<211> LENGTH: 41
<212> TYPE: PRT
<213> ORGANISM: Artificial Sequence
<220> FEATURE:
<221> NAME/KEY: source
<223> OTHER INFORMATION: /note="Description of artificial sequence:
      PPL41 peptide"

<400> SEQUENCE: 6

Pro Glu Val Pro Pro Trp Thr Gly Glu Val Ser Pro Ala Gln Arg Asp
1               5                   10                  15

Gly Gly Ala Leu Gly Gly Gly Gly Arg Gly Pro Trp Asp Ser Ser Asp
            20                  25                  30

Arg Ser Ala Leu Leu Lys Ser Lys Leu
        35                  40
```

```
<210> SEQ ID NO 7
<211> LENGTH: 44
<212> TYPE: PRT
<213> ORGANISM: Artificial Sequence
<220> FEATURE:
<221> NAME/KEY: source
<223> OTHER INFORMATION: /note="Description of artificial sequence:
      PSW44 peptide"

<400> SEQUENCE: 7

Ser Ser Glu Glu His Leu Arg Gln Thr Arg Ser Glu Thr Met Arg Asn
1               5                   10                  15

Ser Val Lys Ser Ser Phe His Asp Pro Lys Leu Lys Gly Lys Pro Ser
            20                  25                  30

Arg Glu Arg Tyr Val Thr His Asn Arg Ala His Trp
        35                  40

<210> SEQ ID NO 8
<211> LENGTH: 33
<212> TYPE: PRT
<213> ORGANISM: Artificial Sequence
<220> FEATURE:
<221> NAME/KEY: source
<223> OTHER INFORMATION: /note="Description of artificial sequence:
      PAY33 peptide"

<400> SEQUENCE: 8

Ala Thr Gln Leu Asp Gly Pro Ala Gly Ala Leu Leu Arg Leu Val
1               5                   10                  15

Gln Leu Ala Gly Ala Pro Glu Pro Phe Glu Pro Ala Gln Pro Asp Ala
            20                  25                  30

Tyr

<210> SEQ ID NO 9
<211> LENGTH: 48
<212> TYPE: PRT
<213> ORGANISM: Artificial
<220> FEATURE:
<221> NAME/KEY: source
<223> OTHER INFORMATION: /note="Description of artificial sequence:
      peptide 45-92"

<400> SEQUENCE: 9

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45

<210> SEQ ID NO 10
<211> LENGTH: 19
<212> TYPE: PRT
<213> ORGANISM: Artificial Sequence
<220> FEATURE:
<221> NAME/KEY: source
<223> OTHER INFORMATION: /note="Description of artificial sequence:
      SPCD19 peptide"

<400> SEQUENCE: 10

Cys Arg Pro Gln Asp Met Lys Gly Ala Ser Arg Ser Pro Glu Asp Ser
1               5                   10                  15

Ser Pro Asp
```

```
-continued

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of artificial sequence:
      PSV11 peptide"

<400> SEQUENCE: 11

Cys Ser Ser Pro Asp Ala Ala Arg Ile Arg Val
1               5                   10
```